United States Patent
Martin

(10) Patent No.: US 7,060,716 B2
(45) Date of Patent: Jun. 13, 2006

(54) TRYPTASE INHIBITORS

(75) Inventor: Thomas Martin, Constance (DE)

(73) Assignee: Altana Pharma AG, Constance (DE)

( * ) Notice: Subject to any disclaimer, the term of this patent is extended or adjusted under 35 U.S.C. 154(b) by 260 days.

(21) Appl. No.: 10/468,216

(22) PCT Filed: Feb. 19, 2002

(86) PCT No.: PCT/EP02/01723

§ 371 (c)(1),
(2), (4) Date: Aug. 18, 2003

(87) PCT Pub. No.: WO02/066430

PCT Pub. Date: Aug. 29, 2002

(65) Prior Publication Data

US 2004/0067943 A1    Apr. 8, 2004

(30) Foreign Application Priority Data

Feb. 21, 2001   (EP) .................................. 01104109

(51) Int. Cl.
*C07D 213/04* (2006.01)
*A61K 31/44* (2006.01)
*A61P 19/02* (2006.01)
*A61P 11/06* (2006.01)

(52) U.S. Cl. .................... 514/336; 546/268.1; 546/348

(58) Field of Classification Search ............. 546/268.1, 546/348; 514/336
See application file for complete search history.

(56) References Cited

U.S. PATENT DOCUMENTS 6,489,327 B1   12/2002   Bär et al.

FOREIGN PATENT DOCUMENTS

| WO | WO 95/32945 | 12/1995 |
|---|---|---|
| WO | WO 96/09297 | 3/1996 |
| WO | WO 98/04537 | 2/1998 |
| WO | WO 99/12918 | 3/1999 |
| WO | WO 99/24395 | 5/1999 |
| WO | WO 99/24407 | 5/1999 |
| WO | WO 99/40073 | 8/1999 |
| WO | WO 99/40083 | 8/1999 |
| WO | WO 00/14097 | 3/2000 |
| WO | WO 01/10845 | 2/2001 |
| WO | WO 01/10848 | 2/2001 |
| WO | WO 01/19809 | 3/2001 |
| WO | WO 01/46128 | 6/2001 |
| WO | WO 01/46168 | 6/2001 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
See Oh et al., Journal of Immunology, 1992-2000, 2002.*
Sommerhoff, American Journal of Respiratory and Critical Care Medicine, 164: 552-558. 2001.*
Krishna, et al., "Inhibition of mast cell tryptase by inhaled APC 366 attenuates allergen-induced late-phase airway obstruction in asthma", *J. Allergy Clin. Immunol.*, Jun., 2001, pp. 1039-1045.
Rice, et al., "Dibasic Inhibitors of human mast cell tryptase. Part 2: Structure-Activity Relationships and Requirements for Potent Activity", Bioorganic & Medicinal Chemistry Letters 10, pp. 2361-2366 (2000).

* cited by examiner

*Primary Examiner*—Venkataraman Balasubramanian
(74) *Attorney, Agent, or Firm*—Nath & Associates; Joshua B. Goldberg; Sheldon M. McGee

(57) ABSTRACT

Compounds of the formula (I), in which M is a central building block selected from the group below in which A1, A2, K1 and K2 are as defined in the description, are novel effective tryptase inhibitors.

12 Claims, No Drawings

TRYPTASE INHIBITORS

APPLICATION OF THE INVENTION

The invention relates to novel tryptase inhibitors which are used in the pharmaceutical industry for preparing medicaments.

KNOWN TECHNICAL BACKGROUND

The international applications WO95/32945 (=U.S. Pat. No. 5,656,660), WO96/09297 (=U.S. Pat. Nos. 6,022,969, 6,221,228), WO98/04537, WO99/12918, WO99/24395, WO99/24407, WO99/40073, WO99/40083 (=DE19851299) and WO00/14097 describe low-molecular-weight bivalent compounds for use as tryptase inhibitors.

DESCRIPTION OF THE INVENTION

It has now been found that the compounds of the formula I, which are described in more detail below, have surprising and particularly advantageous properties. The invention provides compounds of the formula I

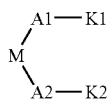

in which

M is a central building block selected from the group below

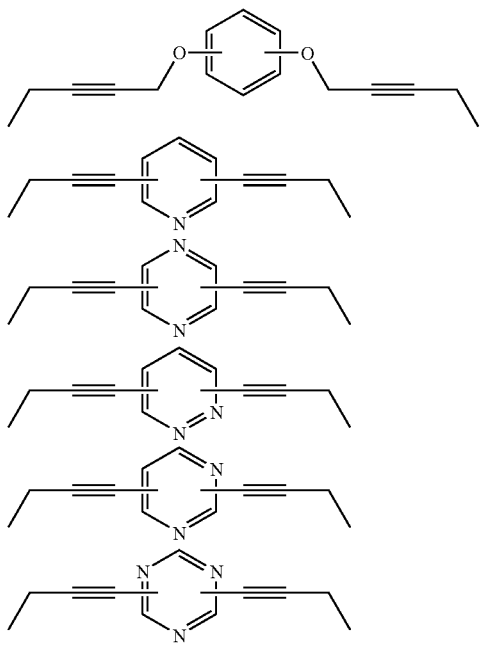

A1 is —O-B1-A3-, -A5-B1-O—, —C(O)—, —C(O)—NH—, —NH—C(O)—, —O—C(O)—NH—, —NH—C(O)—O—, —NH—C(O)—NH— or —O—C(O)—O—,

A2 is —O-B2-A4-, -A6-B2-O—, —C(O)—, —C(O)—NH—, —NH—C(O)—, —O—C(O)—NH—, —NH—C(O)—O—, —NH—C(O)—NH— or —O—C(O)—O—,

A3 and A4 are identical or different and are —C(O)—, —C(O)—NH—, —NH—C(O)—, —O—C(O)—NH—, —NH—C(O)—O—, —NH—C(O)—NH— or —O—C(O)—O—, A5 and A6 are identical or different and are —C(O)—, —C(O)—NH—, —NH—C(O)—, —O—C(O)—NH—, —NH—C(O)—O—, —NH—C(O)—NH— or —O—C(O)—O—, B1 and B2 are identical or different and are 1–4C-alkylene, K1 is -B3-X1, -B3-Y1 or -B3-Z1-B5-X1, K2 is -B4-X2, -B4-Y2 or -B4-Z2-B6-X2, B3 and B4 are identical or different and are a bond or 1–4C-alkylene, B5 and B6 are identical or different and are a bond or 1–2C-alkylene, X1 and X2 are Identical or different and are amino, aminocarbonyl or amidino, Y1 and Y2 are imidazol-1-yl, Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 35, preferably 24 to 29, bonds have to be present, and the salts of these compounds and the N-oxides and their salts, except for all those compounds in which one or more of the variables B3, B4, B5 or B6 can assume the meaning of a bond, resulting in the direct linkage of two heteroatoms.

1–4C-alkylene represents straight-chain or branched 1–4C-alkylene radicals, for example the methylene [—CH$_2$—], ethylene [—CH$_2$—CH$_2$—], trimethylene [—CH$_2$—CH$_2$—CH$_2$—], tetramethylene [—CH$_2$—CH$_2$—CH$_2$—CH$_2$—], 1,2-dimethyethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—] or the 1-methylethylene [—CH(CH$_3$)—CH$_2$—] radical.

By definition, the groups Z1 and Z2 are located between groups B3 and B5 (-B3-Z1-B5-) and B4 and B6 (-B4-Z2-B6-), respectively. Accordingly, in the divalent groupings mentioned by way of example (for example 3,6-indolylene), the first number indicates the point of attachment to the group B3 and B4, respectively, and the second number indicates the point of attachment to the group B5 and B6, respectively.

The groups Z1 and Z2 may inter alia have the meanings 1,4-cyclohexylene and 1,3-cyclohexylene. The invention embraces the compounds of the formula I in which the groups B3, B5 and B4, B6, respectively, are attached (1e,4e), (1a,4a), (1e,4a), (1a,4e), (1e,3e), (1a,3a), (1e,3a) and (1a,3e) to the cyclohexylene radical. In this context, particular preference is given to the (1e,4e) attachment ("e" means equatorial and "a" means axial).

In the context of this application, the term "terminal nitrogen atom" means in each case a nitrogen atom in the groupings designated X1, X2, Y1 and Y2.

If the group X1 or X2 contains only one nitrogen atom, this nitrogen atom is the terminal nitrogen atom.

If the group X1 or X2 contains a plurality of nitrogen atoms, the nitrogen atom which is furthest from the atom by means of which the bond to the group B3 (B5) or B4 (B6) is established is the terminal nitrogen atom.

If the group Y1 or Y2 contains only one nitrogen atom, this ring nitrogen atom is the terminal nitrogen atom.

If the group Y1 or Y2 contains a plurality of nitrogen atoms, the ring nitrogen atom which is furthest from the atom by means of which the bond to the group B3 or B4 is established is the terminal nitrogen atom.

According to the invention, the direct route between the nitrogen atoms which act as terminal nitrogen atoms in the groups defined as X1 (Y1) or X2 (Y2) is considered to be the number of bonds which is obtained by counting the bonds which represent the shortest possible connection between the terminal nitrogen atoms.

The following example is meant to Illustrate the determination of the number of bonds on the direct route between two terminal nitrogen atoms:

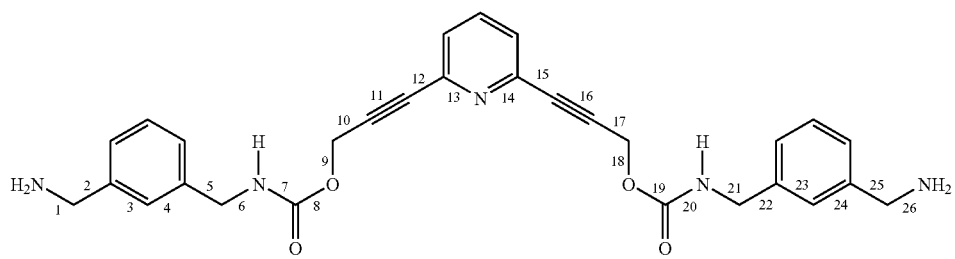

Here, the direct route comprises 26 bonds.

The definitions of M contain chemical formulae, such as, for example,

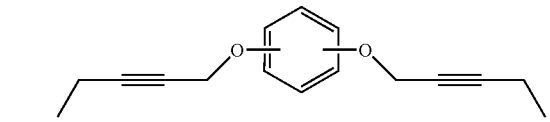

This formula represents 2,6-bis(prop-1-ynyl)pyridine, 2,5-bis(prop-1-ynyl)pyridine, 2,4-bis(prop-1-ynyl)pyridine, 2,3-bis(prop-1-ynyl)pyridine, 3,6-bis(prop-1-ynyl)pyridine, 3,5-bis(prop-1-ynyl)pyridine or 3,4-bis(prop-1-ynyl)pyridine. This applies correspondingly to the other chemical formulae given in the definitions of M.

Preference is given to compounds of the formula I whose molecular weight is below 600 g/mol.

Suitable salts for compounds of the formula I are all acid addition salts. Particular mention may be made of the pharmaceutically acceptable salts of inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically unacceptable salts which can be obtained initially as process products, for example in the preparation of the compounds according to the invention on an industrial scale, are converted into pharmacologically acceptable salts by processes known to the person skilled in the art.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Compounds of the formula I which are to be emphasized are those in which

M is a central building block selected from the group below

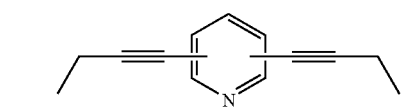

A1 is —O-B1-A3-, -A5-B1-O—, —NH—C(O)—, —O—C(O)—NH—, —NH—C(O)—O—, —NH—C(O)—NH— or —O—C(O)—O—,

A2 is —O-B2-A4-, -A6-B2-O—, —NH—C(O)—, —O—C(O)—NH—, —NH—C(O)—O—, —NH—C(O)—NH— or —O—C(O)—O—,

A3 and A4 are identical or different and are —C(O)—NH—, —NH—C(O)—, —O—C(O)—NH—, —NH—C(O)—O—, —NH—C(O)—NH— or —O—C(O)—O—, A5 and A6 are identical or different and are —NH—C(O)—, —O—C(O)—NH—, —NH—C(O)—O—, —NH—C(O)—NH— or —O—C(O)—O—, B1 and B2 are identical or different and 1–2C-alkylene, K1 is -B3-Z1-B5-X1, K2 is -B4-Z2-B6-X2, B3 and B4 are identical or different and are a bond or 1–2C-alkylene, B5 and B6 are identical or different and are a bond or 1–2C-alkylene, X1 and X2 are identical or different and are amino or amidino, Z1 and Z2 are identical or different and are 1,3-phenylene, 1,4-phenylene, 1,3-cyclohexylene or 1,4-cyclohexylene, and where on the direct route between the terminal nitrogen atoms 20 to 35, preferably 24 to 29, bonds have to be present, and the salts of these compounds, the N-oxides and their salts.

Compounds of the formula I which are to be particularly emphasized are those in which M is a central building block selected from the group below

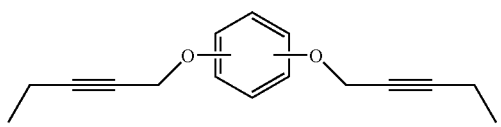

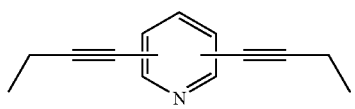

A1 is —O—C(O)—NH—,

A2 is —O—C(O)—NH—,

K1 is -B3-Z1-B5-X1,

K2 is -B4-Z2-B6-X2,

B3 and B4 are identical and are methylene,

B5 and B6 are identical and are methylene,

X1 and X2 are identical and are amino,

Z1 and Z2 are identical or different and are 1,3-phenylene or 1,4-phenylene, and the salts of these compounds, the N-oxides and their salts.

Preferred compounds of the formula I are 2,6-bis-[3-(3-aminomethylbenzylaminocarbonyloxy)prop-1-ynyl]pyridine and 2,6-bis-[3-(4-aminomethylbenzylaminocarbonyloxy)prop-1-ynyl]pyridine and the salts of these compounds, the N-oxides and their salts.

The compounds of the formula I are constructed of a large number of building blocks (M, A1, A2, A3, A4, A5, A6, B1, B2, B3, B4, B5, B6, X1, X2, Y1, Y2, Z1 and Z2). In principle, they can be synthesized starting with any of these building blocks. If the compounds of the formula I are constructed largely symmetrically, it is favorable to start the synthesis with the central building block M, whereas in the case of predominantly asymmetrical compounds of the formula I a synthesis starting with one of the end groups K1 or K2 may be advantageous.

Suitable starting materials for synthesizing the compounds of the formula I according to the invention are, for example, 2,6-dibromopyridine, 2,5-dibromopyridine, 3,5-dibromopyridine, 2,5-dibromopyridazine, 2,4-dibromopyrimidine, 2,4-dibromo-[1,3,5]-triazine or 1,3-dihydroxybenzene.

Here, the building blocks are linked using always the same pattern, known per se to the person skilled in the art.

It is known to the person skilled in the art that the compounds of the formula I can either be synthesized building block by building block, or by initially constructing relatively large fragments consisting of several individual building blocks, which can then be joined to give the complete molecule.

Owing to the meanings which the individual building blocks of the compounds of the formula I can assume, ether [—O—], keto [—C(O)—], amide [—C(O)—NH—, —NH—C(O)—], carbamate [—NH—C(O)—O—, —O—C(O)—NH—], carbamide [—NH—C(O)—NH—] or carbonate [—O—C(O)—O—] bridges can be present in the compounds of the formula I.

How to prepare such bridges is known per se to the person skilled in the art; suitable methods and starting materials for their preparation are described, for example, in March, Advanced Organic Chemistry, Reactions, Mechanisms and Structure, Third Edition, 1985, John Wiley & Sons.

Ether bridges can be prepared, for example, by the method of Williamson.

Keto bridges can be introduced, for example, as a component of relatively large building blocks, such as, for example, carboxylic acid derivatives.

There is also a large number of known methods for preparing amide bridges. An example which may be mentioned here is the reaction of acyl chlorides with primary or secondary amines. Furthermore, reference is also made to all the methods which have been developed for peptide chemistry.

Carbamate bridges can be prepared, for example, by reacting chloroformates with amines. The chloroformates for their part can be synthesized from alcohols and phosgene. A further variant for constructing carbamate bridges is the addition of alcohols to isocyanates. Similarly to carbamate bridges, it is possible to prepare carbonate bridges starting from chloroformates, by reaction with alcohols (instead of amines).

Carbamide bridges can be prepared, for example, by reacting isocyanates with amines.

The preparation of the compounds of the formula I may be shown in an exemplary manner using the reaction schemes below. Reaction scheme 1 shows the preparation of the exemplary compounds 1 and 2. Other compounds of the formula I can be prepared analogously, or by using the abovementioned methods known per se to the person skilled in the art.

Reaction scheme 1:

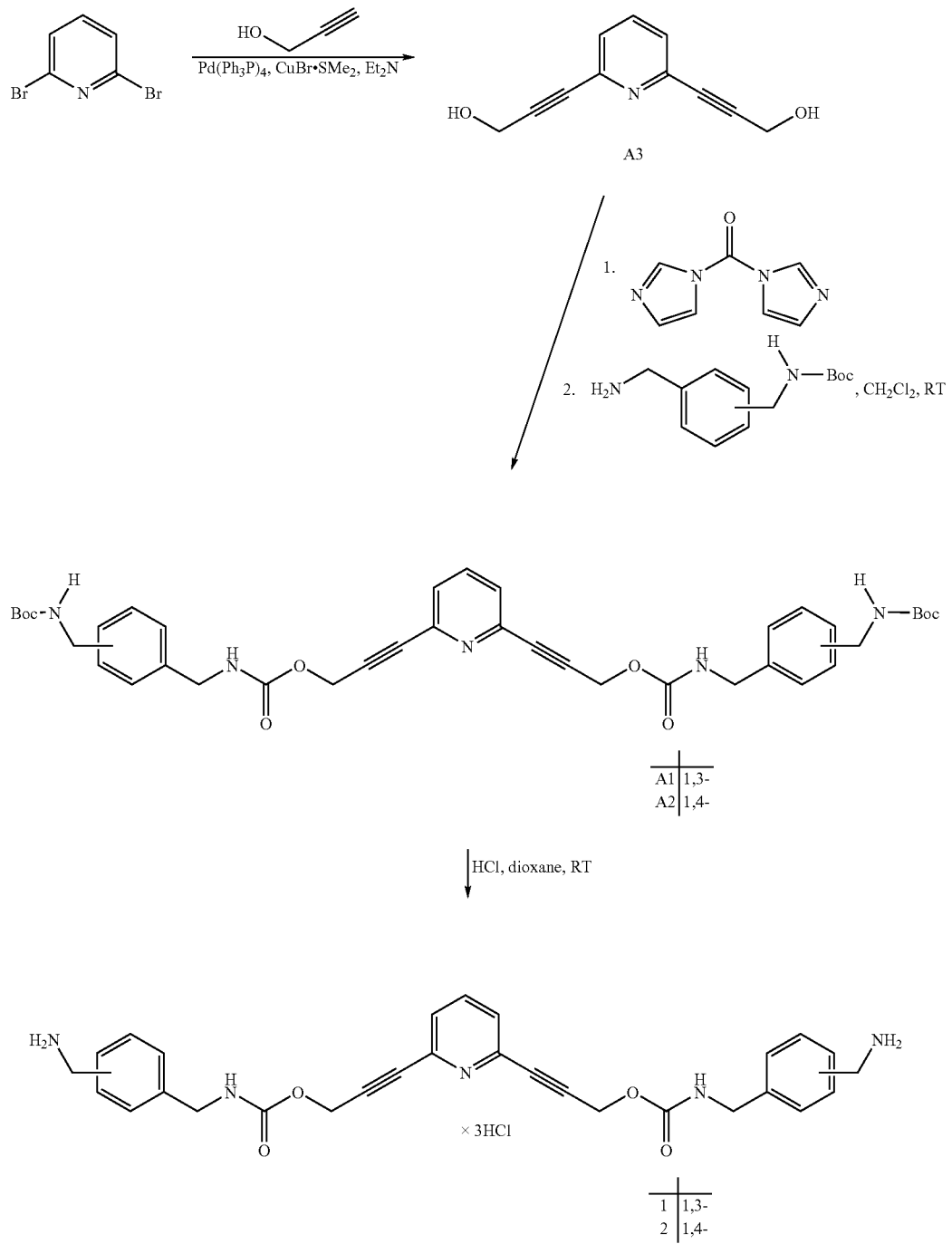

It is also possible to convert compounds of the formula I by derivatization into other compounds of the formula I. Thus, for example, compounds of the formula I having a nitrogen-containing heteroaryl, heteroarylene or heterocycloalkylene building block can be converted by oxidation into the corresponding N-oxides.

The N-oxidation is carried out in a manner which is likewise known to the person skilled in the art, for example using hydrogen peroxide in methanol or m-chloroperoxybenzoic acid in dichloromethane at room temperature. Which reaction conditions are required in the particular case for carrying out the process is known to the person skilled In the art owing to his expert knowledge.

It is furthermore known to the person skilled in the art that if there are a number of reactive centers of a starting material or intermediate, it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent under reduced pressure and recrystallizing the resulting residue from a suitable solvent or subjecting It to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

The examples below serve to illustrate the invention in more detail without restricting it. Likewise, further compounds of the formula I, whose preparation is not explicitly described, can be prepared in an analogous manner or in a manner familiar per se to the person skilled in the art using customary process techniques.

In the examples below, the abbreviation RT stands for room temperature, calc. for calculated and MS for mass spectrometry. The compounds mentioned by way of example and their salts are the preferred subject of the invention.

EXAMPLES

End Products

General Procedure

A solution of the Boc-protected divalent compound (A1, A2; 1.0 mmol) in question in $CH_2Cl_2$ (2 ml) is admixed with trifluoroacetic acid (14 ml) and stirred at RT for 1 h. A saturated solution of HCl in diethyl ether (10 ml) is then added dropwise to the reaction mixture. The resulting precipitate is immediately filtered off and washed with diethyl ether (3×5 ml). Drying under reduced pressure gives the title compounds (end products 1 and 2) as colorless solids.

1. 2,6-Bis-[3-(3-aminomethylbenzylaminocarbonyloxy)prop-1-ynyl]pyridine trihydrochloride

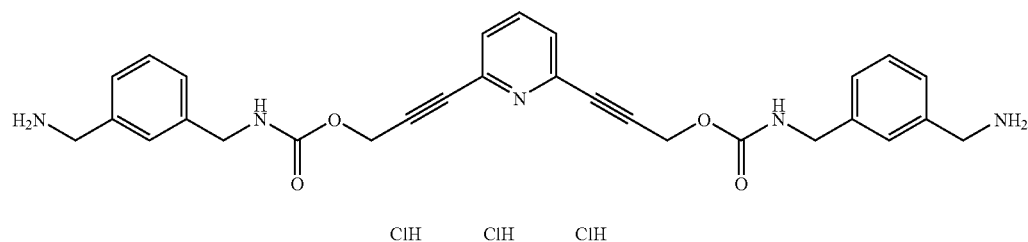

MS: calc.: $C_{29}H_{29}N_5O_4$ (511.6), found: [MH$^+$] 512.3

2. 2,6-Bis-[3-(4-aminomethylbenzylaminocarbonyloxy)prop-1-ynyl]pyridine trihydrochloride

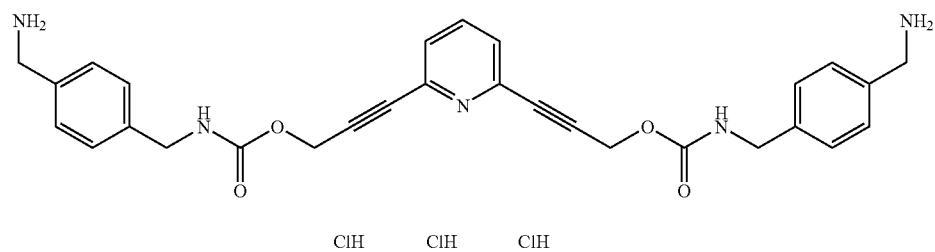

MS: calc.: $C_{29}H_{29}N_5O_4$ (511.6), found: [MH$^+$] 512.3

Starting Materials

A1. 2,6-Bis-[3-(3-N-tert-butoxycarbonylaminomethylbenzylaminocarbonyloxy)prop-1-ynyl]pyridine N,N-carbonyldiimidazole (1.04 g, 8.15 mmol) is added to a solution of 2,6-bis-(3-hydroxyprop-1-ynyl)pyridine (A3, 0.5 g, 2.7 mmol) in absolute $CH_2Cl_2$ (12 ml), and the mixture is stirred at RT for 2.5 h. The reaction solution is diluted with $CH_2Cl_2$ (12 ml) and extracted with a semisaturated aqueous NaCl solution (25 ml). The organic phase is dried over $MgSO_4$, filtered off and concentrated under reduced pressure. The resulting residue is taken up in absolute CH₂Cl₂ (12 ml), 3-(tert-butyloxycarbonylaminomethyl)benzylamine (1.28 g, 5.4 mmol) is added and the mixture is stirred at RT overnight. The reaction solution is diluted with CH₂Cl₂ (12 ml) and extracted with a semisaturated aqueous NaCl solution (25 ml). The organic phase is dried over MgSO₄, filtered off and concentrated under reduced pressure. Further purification is carried out by chromatography [toluene/acetone (7.5:2.5)] on a silica gel column. This gives the title compound (1.0 g) as a colorless solid. TLC, silica gel (glass plates), [toluene/acetone (7:3)], $R_f$=0.47.

MS: calc.: $C_{39}H_{45}N_5O_8$ (711.8), found: [MH⁺] 712.0; [MNa⁺] 734.3

A2. 2,6-Bis-[3-(4-N-tert-butoxycarbonylaminomethylbenzylaminocarbonyl-3-oxy)prop-1-ynyl]pyridine N,N-carbonyldiimidazole (1.04 g, 8.15 mmol) is added to a solution of 2,6-bis-(3-hydroxyprop-1-ynyl)pyridine (A3, 0.5 g, 2.7 mmol) in absolute CH₂Cl₂ (12 ml), and the mixture is stirred at RT for 2.5 h. The reaction solution is diluted with CH₂Cl₂ (12 ml) and extracted with a semisaturated aqueous NaCl solution (25 ml). The organic phase is dried over MgSO₄, filtered off and concentrated under reduced pressure. The resulting residue is taken up in absolute CH₂Cl₂ (12 ml), 4-(tert-butyloxycarbonylaminomethyl)benzylamine (1.28 g, 5.4 mmol) is added and the mixture is stirred at RT overnight. Diethyl ether (20 ml) is added to the reaction solution and the resulting precipitate is filtered off, washed with diethyl ether (15 ml) and dried. This gives the title compound (1.0 g) as a colorless solid. TLC, silica gel (glass plates), [toluene/acetone (7:3)], $R_f$=0.43.

MS: calc.: $C_{39}H_{45}N_5O_8$ (711.8), found: [MH⁺] 712.0; [MNa+] 734.3

A3. 2,6-Bis-(3-hydroxyprop-1-ynyl)pyridine

Pd(Ph₃P)₄ (99 mg, 2%), CuBrSMe₂ (38 mg) and propargyl alcohol (1.3 ml, 21 mmol) are added successively to a solution of 2,6-dibromopyridine (5.0 g, 21.1 mmol) in triethylamine (120 ml), and the mixture is stirred at RT for 10 min and then under reflux at 80° C. for 2 h. After cooling, the reaction mixture is filtered off through kieselguhr, and the filter cake is washed with ethyl acetate (20 ml). The organic phase is concentrated under reduced pressure. Further purification is carried out by chromatography [toluene/acetone (7:3)] on a silica gel column. This gives the title compound (2.65 g) as a colorless solid. TLC, silica gel (glass plates) [toluene/acetone (7:3)], $R_f$=0.15.

MS: calc.: $C_{11}H_9NO_2$ (187.2), found: [MH⁺] 188.0

Commercial Utility

As tryptase inhibitors, the compounds according to the invention have useful pharmacological properties which make them commercially utilizable. Human tryptase is a serin protease which is the main protein in human mast cells. Tryptase comprises eight closely related enzymes (α1, α2, β1a, β1b, β2, β3, mMCP-7-like-1, mMCP-7-like-2; 85 to 99% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815; Pallaoro et al., J. Biol. Chem. 274 (1999) 3355–3362). However, only the β-tryptases (Schwartz et al., J. Clin. Invest. 96 (1995) 2702–2710; Sakai et al., J. Clin. Invest. 97 (1996) 988–995) are activated intracellularly and stored in catalytically active form in secretory granules. Compared with other known serin proteases, such as, for example, trypsin or chymotrypsin, tryptase has some special properties (Schwartz et al., Methods Enzymol. 244, (1994), 88–100; G. H. Caughey, "Mast cell proteases in immunology and biology". Marcel Dekker, Inc., New York, 1995). Tryptase from human tissue has a noncovalently-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly since an increased tryptase concentration was observed in a number of disorders of this type. Thus, tryptase is associated, inter alia, with the following diseases: acute and chronic (in particular inflammatory and allergen-induced) airway disorders of various origins (for example bronchitis, allergic bronchitis, bronchial asthma, COPD); interstitial lung disorders; disorders based on allergic reactions of the upper airways, (pharynx, nose) and the adjacent regions (for example paranasal sinuses, conjunctivae), such as, for example, allergic conjunctivitis and allergic rhinitis; disorders of the arthritis type (for example rheumatoid arthritis); autoimmune disorders, such as multiple sclerosis; furthermore neurogenic inflammations, arteriolosclerosis and cancer; moreover periodontitis, anaphylaxis, interstitial cystitis, dermatitis, psoriasis, sclerodermia/systemic sclerosis, inflammatory intestinal disorders (Crohn's disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, Chapter 3.3.1–3.3.23).

A further subject of the invention are the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by processes which are known per se and are familiar to the person skilled in the art. As medicaments, the compounds according to the invention (=active compounds) are either employed as such, or preferably in combination with suitable pharmaceutical excipients, for example in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of diseases of the respiratory tract, the compounds according to the invention are preferably also administered by inhalation, preferably in the form of an aerosol, with the aerosol particles of solid, liquid or mixed composition having a diameter of from 0.5 to 10 µm, advantageously of from 2 to 6 µm.

The aerosol can be produced, for example, using pressure-driven nozzle nebulizers or ultrasonic nebulizers, advantageously, however, using propellant gas-driven metered aerosols or by means of the propellant gas-free use of micronized active compounds from inhalation capsules.

Depending on the inhalation system employed, the administration forms also contain, In addition to the active compounds, the requisite auxiliary substances, for example propellant gases (e.g. Frigen in the case of metered aerosols), surface-active substances, emulsifiers, stabilizers, preservatives, aromatizing agents, fillers (e.g. lactose in the case of powder inhalers) and, where appropriate, additional active compounds.

For the purposes of inhalation, a large number of appliances are available which can be used to generate aerosols of optimal particle size and administer them using an inhalation technique which is as appropriate as possible for the patient. In addition to using attachments (spacers and expanders) and pear-shaped containers (e.g. Nebulator® and Volumatic®), and also automatic spray puff releasers (Autohaler®) for metered aerosols, a number of technical solutions are available, particularly in the case of the powder inhalers (e.g. Diskhaler®, Rotadisk®, Turbohaler® or the inhaler described in European patent application 0 505 321), which technical solutions can be used to achieve optimal administration of the active compound.

For the treatment of dermatoses, the compounds according to the invention are in particular used In the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram per day.

Biological Investigations

The documented pathophysiological effects of mast cell tryptase are caused directly by the enzymatic activity of the protease. Accordingly, they are reduced or blocked by inhibitors which inhibit the enzymatic activity of the tryptase. A suitable measure for the affinity of a reversible inhibitor to the target protease is the equilibrium dissociation constant $K_i$ of the enzyme-inhibitor complex. This $K_i$ value can be determined via the effect of the inhibitor on the tryptase-induced cleavage of a chromogenic peptide-p-nitroanilide substrate or a fluorogenic peptide-aminomethylcoumarin substrate.

Methodology

The dissociation constants for the tryptase-inhibitor complexes are determined under equilibrium conditions in accordance with the general proposals of Bieth (Bieth J G, Pathophysiological Interpretation of kinetic constants of protease inhibitors, Bull. Europ. Physiopath. Resp. 16:183–195, 1980) and the methods of Sommerhoff et al. (Sommerhoff C P et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is isolated from lung tissue or prepared recombinantly; the specific activity of the protease, determined by titration, is usually greater than 85% of the theoretical value. In the presence of heparin (0.1–50 µg/ml) for stabilizing the protease, constant amounts of the tryptase are incubated with increasing amounts of the inhibitors. After an equilibrium between the reaction partners has formed, the remaining enzyme activity after addition of the peptide-p-nitroanilide substrate tos-GlyPro-arg-pNA is determined and the cleavage of the latter is monitored at 405 nm for 3 min. Alternatively, the remaining enzymatic activity can also be determined using fluorogenic substrates. The apparent dissociation constants $K_{iapp}$ (i.e. in the presence of substrate) are subsequently determined by adapting the enzyme rates to the general equation for reversible inhibitors (Morrison J F, Kinetics of the reversible inhibition of enzyme-catalyzed reactions by tight-binding inhibitors, Biochim. Biophys. Acta 185,269–286,1969) using non-linear regression:

$$V_1/V_0 = 1 - \{E_t + I_t + K_{iapp} - [(E_t + I_t + K_{iapp})^2 - 4E_t I_t]^{1/2}\}/2E_t$$

$V_1$ and $V_0$ are the rates in the presence and absence, respectively, of the inhibitor, and $E_t$ and $I_t$ are the tryptase and inhibitor concentrations, respectively.

The apparent dissociation constants determined for the compounds according to the invention are shown in Table A below, where the numbers of the compounds correspond to the numbers of the compounds in the examples.

TABLE A

| Inhibition of human tryptase | |
|---|---|
| Compound | $K_{Iapp}$ (µM) |
| 1 | 0.0026 |
| 2 | 0.006 |

The invention claimed is:

1. A compound of formula I $$\begin{array}{c} A1—K1 \\ / \\ M \\ \backslash \\ A2—K2 \end{array} \quad (I)$$

in which

M is a central building block

[pyridine ring structure with two alkyne substituents]

A1 is —O-B1-A3-, -A5-B1-O—, —C(O)—, —C(O)—NH—, —NH—C(O)—, —O—C(O)—NH—, —NH—C(O)—O—, —NH—C(O)—NH— or —O—C(O)—O—,

A2 is —O—B2-A4-, -A6-B2-O—, —C(O)—, —C(O)—NH—, —NH—C(O)—, —O—C(O)—NH—, —NH—C(O)—O—, —NH—C(O)—NH— or —O—C(O)—O—,

A3 and A4 are identical or different and are —C(O)—, —C(O)—NH—, —NH—C(O)—, —O—C(O)—NH—, —NH—C(O)—O—, —NH—C(O)—NH— or —O—C(O)—O—, A5 and A6 are identical or different and are —C(O)—, —C(O)—NH—, —NH—C(O)—, —O—C(O)—NH—, —NH—C(O)—O—, —NH—C(O)—NH— or —O—C(O)—O—, B1 and B2 are identical or different and are 1–4C-alkylene, K1 is -B3-X1, B3-Y1 or -B3-Z1-B5-X1, K2 is -B4-X2, -B4-Y2 or -B4-Z2-B6-X2, B3 and B4 are identical or different and are a bond or 1–4C-alkylene, B5 and B6 are identical or different and are a bond or 1–2C-alkylene, X1 and X2 are identical or different and are amino, aminocarbonyl or amidino, Y1 and Y2 are imidazol-1-yl, Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 35 bonds have to be present, or a salt, N-oxide or salt of an N-oxide thereof except for all those compounds in which one or more of the variables B3, B4, B5 or B6 can assume the meaning of a bond, resulting in the direct linkage of two heteroatoms.

2. A compound of the formula I as claimed in claim 1 in which

M is a central building block

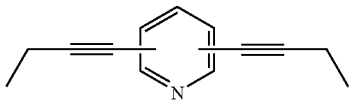

A1 is —O-B1-A3-, -A5-B1-O—, —NH—C(O)—, —O—C(O)—NH—, —NH—C(O)—O—, —NH—C(O)—NH— or —O—C(O)—O—,

A2 is —O-B2-A4-, -A6-B2-O—, —NH—C(O)—, —O—C(O)—NH—, —NH—C(O)—O—, —NH—C(O)—NH— or —O—C(O)—O—,

A3 and A4 are identical or different and are —C(O)—NH—, —NH—C(O)—, —O—C(O)—NH—, —NH—C(O)—O—, —NH—C(O)—NH— or —O—C(O)—O—, A5 and A6 are identical or different and are —NH—C(O)—O—C(O)—NH—, —NH—C(O)—O—, —NH—C(O)—NH— or —O—C(O)—O—, B1 and B2 are identical or different and are 1–2C-alkylene, K1 is -B3-Z1-B5-X1, K2 is -B4-Z2-B6-X2, B3 and B4 are identical or different and are a bond or 1–2C-alkylene, B5 and B6 are identical or different and are a bond or 1–2C-alkylene, X1 and X2 are identical or different and are amino or amidino, Z1 and Z2 are identical or different and are 1,3-phenylene, 1,4-phenylene, 1,3-cyclohexylene or 1,4-cyclohexylene, and where on the direct route between the terminal nitrogen atoms 20 to 35 bonds have to be present, or a salt, N-oxide or salt of an N-oxide thereof.

3. A compound of the formula I as claimed in claim 1 in which

M is a central building block

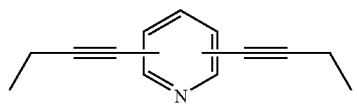

A1 is —O—C(O)—NH—,

A2 is —O—C(O)—NH—,

K1 is -B3-Z1-B5-X1,

K2 is -B4-Z2-B6-X2,

B3 and B4 are identical and are methylene,

B5 and B6 are identical and are methylene,

X1 and X2 are identical and are amino,

Z1 and Z2 are identical or different and are 1,3-phenylene or 1,4-phenylene, or a salt, N-oxide or salt of an N-oxide thereof.

4. A compound of the formula I as claimed in claim 1 having the chemical name 2,6-bis-[3-(3-aminomethylbenzylaminocarbonyloxy)prop-1-ynyl]pyridine or 2,6-bis-[3-(4-aminomethylbenzylaminocarbonyloxy)prop-1-ynyl]pyridine or a salt, N-oxide or salt of an N-oxide thereof.

5. A compound of the formula I as claimed in claim 1 where on the direct route between the terminal nitrogen atoms 24 to 29 bonds are present.

6. A compound of the formula I as claimed claim 1 having a molecular weight of below 600 g/mol.

7. A method of treating a disease or disorder in a patient comprising administering to a patient in need thereof a therapeutically effective amount of one or more compounds of the formula I as claimed in claim 1 or a salt, N-oxide or salt of an N-oxide thereof, wherein the disease or disorder is selected from the group consisting of asthma, allergic conjunctivitis, allergic rhinitis, psoriasis, sclerodermatitis and inflammatory bowel disease.

8. A pharmaceutical composition comprising one or more compounds of the formula I as claimed in claim 1 or a salt, N-oxide or salt of an N-oxide thereof, together with a pharmaceutical excipient.

9. A method of treating asthma in a patient comprising administering to a patient in need thereof a therapeutically effective amount of one or more compounds of the formula I as claimed in claim 1 or a salt, N-oxide or salt of an N-oxide thereof.

10. A compound as claimed in claim 2 where on the direct route between the terminal nitrogen atoms 24 to 29 bonds are present.

11. A compound as claimed in claim 2 having a molecular weight of below 600 g/mol.

12. A compound as claimed in claim 3 having a molecular weight of below 600 g/mol.

* * * * *

UNITED STATES PATENT AND TRADEMARK OFFICE
CERTIFICATE OF CORRECTION

PATENT NO.        : 7,060,716 B2
APPLICATION NO. : 10/468216
DATED             : June 13, 2006
INVENTOR(S)       : Martin It is certified that error appears in the above-identified patent and that said Letters Patent is hereby corrected as shown below:

Claim 2, Column 15, Line 52, Please delete " -NH-C (O) -, -O-C (O) -NH-,"
and replace with -- -NH-C (O) -, -O-C (O) -NH-, --

Claim 2, Column 15, Lines 55-56, Please delete "-NH-C (O) –O-C (O) -NH-," and replace with -- -NH-C (O) -, -O-C (O) -NH-, --

Signed and Sealed this

Fifteenth Day of August, 2006

JON W. DUDAS
*Director of the United States Patent and Trademark Office*